United States Patent
Prokhnevsky et al.

(10) Patent No.: US 9,364,530 B2
(45) Date of Patent: Jun. 14, 2016

(54) VIRUS-LIKE PARTICLES COMPRISING A MATRIX PROTEIN FROM A PLANT ENVELOPED VIRUS AND USES THEREOF

(71) Applicant: FRAUNHOFER USA Inc., Newark, DE (US)

(72) Inventors: Alexei Prokhnevsky, Wilmington, DE (US); Vidadi Yusibov, Havertown, PA (US)

(73) Assignee: Fraunhofer USA, Inc., Newark, DE (US)

( * ) Notice: Subject to any disclaimer, the term of this patent is extended or adjusted under 35 U.S.C. 154(b) by 0 days.

(21) Appl. No.: 14/379,408

(22) PCT Filed: Mar. 15, 2013

(86) PCT No.: PCT/US2013/032096
§ 371 (c)(1),
(2) Date: Aug. 18, 2014

(87) PCT Pub. No.: WO2013/142329
PCT Pub. Date: Sep. 26, 2013

(65) Prior Publication Data
US 2015/0086589 A1    Mar. 26, 2015

Related U.S. Application Data

(60) Provisional application No. 61/614,141, filed on Mar. 22, 2012.

(51) Int. Cl.
| | |
|---|---|
| *A61K 39/205* | (2006.01) |
| *A61K 39/145* | (2006.01) |
| *C07K 14/005* | (2006.01) |
| *C12N 7/00* | (2006.01) |
| *C12N 15/82* | (2006.01) |
| *C12P 21/02* | (2006.01) |
| *A61K 39/12* | (2006.01) |
| *A61K 39/00* | (2006.01) |

(52) U.S. Cl.
CPC .............. *A61K 39/145* (2013.01); *A61K 39/12* (2013.01); *C07K 14/005* (2013.01); *C12N 7/00* (2013.01); *C12N 15/8203* (2013.01); *C12N 15/8257* (2013.01); *C12P 21/02* (2013.01); *A61K 2039/5258* (2013.01); *C07K 2319/02* (2013.01); *C12N 2760/16122* (2013.01); *C12N 2760/16134* (2013.01); *C12N 2760/16151* (2013.01); *C12N 2760/16222* (2013.01); *C12N 2760/16234* (2013.01); *C12N 2760/20023* (2013.01); *C12N 2760/20041* (2013.01); *C12N 2770/00044* (2013.01)

(58) Field of Classification Search
CPC ............. C07K 14/005; C07K 2319/00; C12N 2770/34034; C12N 2810/10; C12N 2740/16023; C12N 2740/16051; C12N 2760/14123; C12N 2770/00044; C12N 2770/16034; C12N 2770/16051; C12N 2770/18031; C12N 2770/20
See application file for complete search history.

(56) References Cited

U.S. PATENT DOCUMENTS

| | | | |
|---|---|---|---|
| 7,556,940 B2 | 7/2009 | Galarza et al. | |
| 7,763,450 B2 | 7/2010 | Robinson et al. | |
| 8,093,033 B2 | 1/2012 | Kemble et al. | |
| 2010/0111996 A1* | 5/2010 | Leclerc | 424/202.1 |
| 2011/0212128 A1 | 9/2011 | Galarza et al. | |
| 2011/0293650 A1 | 12/2011 | D'Aoust et al. | |
| 2012/0034253 A1 | 2/2012 | Yusibov et al. | |
| 2012/0178149 A1* | 7/2012 | Vezina | A61K 39/145 435/272 |

FOREIGN PATENT DOCUMENTS

| | | | |
|---|---|---|---|
| WO | WO 2007/011904 | * | 11/2007 |
| WO | WO 2008/058396 A1 | | 5/2008 |
| WO | WO 2011/035004 A1 | | 3/2011 |
| WO | WO 2011/035422 A1 | * | 3/2011 |

OTHER PUBLICATIONS

Marusic et al. Journal of Virology, 2001, vol. 75, No. 18, pp. 8434-8439.*
Suinsbury Annu. Rev. Phyopathol. 2010, vol. 48, pp. 437-455.*
Denis et al. Virology, 2007, vol. 363, No. 1, pp. 59-68.*
Cheng et al., Virology, 413:153-60 (2011).
Coronel et al., Journal of Virology, 73(8):7035-38 (1999).
D'Aoust et al., Plant Biotechnology Journal, 6:930-40 (2008).
D'Aoust et al., Plant Biotechnology Journal, 8:607-19 (2010).
Jackson et al., Annu. Rev. Phytopathol, 43:623-60 (2005).
Landry et al., PLoS ONE, 5(12):1-12 (2010).
Nayak et al., Virus Res., 143(2):1-31 (2009).
Pan et al., Journal of Biomedicine and Biotechnology, 11 pages (2010).
PCT/US2013/032096 International Search Report by Birgit Sommer of European Patent Office, mailed Jun. 28, 2013.
Pushko et al., Vaccine, 23:5751-59 (2005).
Vezina et al., BioPharm International, 24(5):s27-s30 (2011).
First Office Action mailed Sep. 28, 2015 in Chinese Application No. 201380014180.2 (with English translation).

(Continued)

*Primary Examiner* — Bao Li
(74) *Attorney, Agent, or Firm* — RatnerPrestia

(57) ABSTRACT

The present invention relates to novel virus-like particles (VLPs) comprising a matrix protein derived from a first plant enveloped virus and a surface polypeptide. The surface polypeptide comprises (a) a surface exposed portion derived from a target polypeptide (b) a transmembrane domain, and (c) a cytosolic tail derived from a transmembrane (e.g., glycoprotein) of a second plant enveloped virus. The target polypeptide may be antigenic or therapeutic. The first and the second plant enveloped viruses may be the same. Either plant enveloped virus may be a plant rhabdovirus. Also provided are methods of making and using the VLPs.

22 Claims, 9 Drawing Sheets

(56) References Cited

OTHER PUBLICATIONS

Ivanov et al., Virus Res. 162(1-2):126-37 (2011).
Taubenberger and Morens, Annu. Rev. Pathol. 3:499-522 (2008).
Jang et al., Viruses 6(8):3159-80 (2014).
Bullough et al., Nature 371:37-43 (1994).
Skehel et al., Proc. Natl. Acad. Sci. USA 79, 968-972 (1982).
Pushko et al., Intervirology 56:141-65 (2013).
A. Zeltins, Mol. Biotechnol. doi:10.1007/s12033-012-9598-4 (2012).
Liu et al., Protein Expression and Purification 90:104-16 (2013).
Yamaji et al., Appl. Microbiol. Biotechnol. 97:1071-9 (2013).
Pillet et al., Vaccine, http://dx.doi.org/10.1016/j.vaccine.2015.09.065 (2015).
Pushko et al., Vaccine, doi:10.1016/j.vaccine.2011.06.068 (2011).
Smith et al., Vaccine, http://dx.doi.org/10.1016/j.vaccine.2013.07.043 (2013).

* cited by examiner

Figure 3

LB  2Enx35S  L-Pro  MET         HEL  POL        Nos  RB

Matrix proteins (M) from plant rhabdoviruses:

-Lettuce Necrotic Yellows Virus (LNYV)             HAi-TM      $M_{LNYV}$ or $M_{NCMV}$ -Northern Cereal Mosaic Virus (NCMV)

Figure 4

LB  2Enx35S  L-Pro  MET         HEL  POL        Nos  RB

Matrix proteins (M) from plant rhabdovirus:

-Lettuce Necrotic Yellows Virus (LNYV)             $HAi-TM(G)_{LNYV}$     $M_{LNYV}$

A. HAi-TM (SEQ ID NO: 1)

MGFVLFSQLPSFLLVSTLLLFLVISHSCRADQICIGYHANNSTEQVDTI
MEKNVTVTHAQDILEKTHNGKLCDLDGVKPLILRDCSVAGWLLGNPM
CDEFINVPEWSYIVEKANPTNDLCYPGSFNDYEELKHLLSRINHFEKIL
IIPKSSWSDHEASSGVSSACPYLGSPSFFRNVVWLIKKNSTYPTIKKS
YNNTNQEDLLVLWGIHPNDAAEQTRLYQNPTTYISIGTSTLNQRLVPK
IATRSKVNGQSGRMEFFWTILKPNDAINFESNGNFIAPEYAYKIVKKG
DSAIMKSELEYGNCNTKCQTPMGAINSSMPFHNIHPLTIGECPKYVKS
NRLVLATGLRNSPQRESRRKKRGLFGAIAGFIEGGWQGMVDGWYGY
HHSNEQGSGYAADKESTQKAIDGVTNKVNSIIDKMNTQFEAVGREF
NNLERRIENLNKKMEDGFLDVWTYNAELLVLMENERTLDFHDSNVKN
LYDKVRLQLRDNAKELGNGCFEFYHKCDNECMESIRNGTYNYPQYSE
EARLKREEISGVKLESIGTYQILSIYSTVASSLALAIMMAGLSLW*M*
*CSNGSLQCRICI**

B. HAi-TM(G)$_{LNYV}$ (SEQ ID NO: 2)

MGFVLFSQLPSFLLVSTLLLFLVISHSCRADQICIGYHANNSTEQVDTI
MEKNVTVTHAQDILEKTHNGKLCDLDGVKPLILRDCSVAGWLLGNPM
CDEFINVPEWSYIVEKANPTNDLCYPGSFNDYEELKHLLSRINHFEKIL
IIPKSSWSDHEASSGVSSACPYLGSPSFFRNVVWLIKKNSTYPTIKKS
YNNTNQEDLLVLWGIHHPNDAAEQTRLYQNPTTYISIGTSTLNQRLVP
KIATRSKVNGQSGRMEFFWTILKPNDAINFESNGNFIAPEYAYKIVKK
GDSAIMKSELEYGNCNTKCQTPMGAINSSMPFHNIHPLTIGECPKYVK
SNRLVLATGLRNSPQRESRRKKRGLFGAIAGFIEGGWQGMVDGWYG
YHHSNEQGSGYAADKESTQKAIDGVTNKVNSIIDKMNTQFEAVGREF
NNLERRIENLNKKMEDGFLDVWTYNAELLVLMENERTLDFHDSNVKN
LYDKVRLQLRDNAKELGNGCFEFYHKCDNECMESIRNGTYNYPQYSE
EARLKREEISGVKLESIGTYQIVTLWATVFLTLGALVAGAKVWEI*M*
*RKANRKSQYKRTNTEPHDSQATWI**

Figure 12

A. M$_{LNYV}$ (SEQ ID NO: 3)

SAKLNWYRITFNDTVWRFDTARGPKDGETCPLIASELFSSGLSEVFKS
VTSFSEILRNMESRGYITNITLRADSDILGPGALRCEFLFPSEVFIPTSH
TLKMGRSSLILEPHLVVLKECKYISSGKLDIGISSIEATSVAVLRRVKGP
AFIGCMDDNPFGVLTKKPSDEKNVLASK*

B. M1 protein (SEQ ID NO: 4)

MSLLTEVETYVLSIVPSGPLKAEIAQRLEDVFAGKNTDLEALMEWLKTR
PILSPLTKGILGFVFTLTVPSERGLQRRRFVQNALNGNGDPNNMDRAV
KLYKKLKREITFHGAKEVALSYSTGALASCMGLIYNRMGTVTTEVAFG
LVCATCEQIADSQHRSHRQMATTTNPLIRHENRMVLASTTAKAMEQM
AGSSEQAAEAMEVASQARQMVQAMRTIGTHPSSSAGLKDNLLENLQ
AYQKRMGVQMQRFK*

US 9,364,530 B2

VIRUS-LIKE PARTICLES COMPRISING A MATRIX PROTEIN FROM A PLANT ENVELOPED VIRUS AND USES THEREOF

CROSS-REFERENCE TO RELATED APPLICATION

This application is a U.S. national phase application of International Application No. PCT/US2013/032096, filed Mar. 15, 2013 claiming the benefit of U.S. Provisional Application No. 61/614,141, filed Mar. 22, 2012, the content of each of which is incorporated herein by its entirety for all purposes.

FIELD OF THE INVENTION

The present invention relates generally to enveloped virus-like particles (VLPs) preferably produced in plants, and methods for making and using the VLPs.

BACKGROUND OF THE INVENTION

Virus-like particles (VLPs) are complex structures formed by self-assembling viral proteins without the presence of the viral genome. The VLP platform is increasingly used to enhance target-specific immunogenicity. VLPs can be produced in several expression systems, including plants. Production of VLPs in plants offers additional advantages, including safety and time efficiency. However, formation of VLPs in plants is part of a physiological process and results in formation of particles of various sizes and shapes, making commercial manufacturing and a smooth regulatory path highly challenging. The size of wild-type influenza virus particles depends on the strain and varies between 70 and 270 nm (Nayak et al., 2009, *Virus Res* 143(2):147-161). Plant-produced influenza viral particles (VLPs) have different shapes and a broad size range. For example, enveloped pleiomorphic influenza VLPs have been reported to be 100 to 150 nm in size. (Vezina et al., 2011, *BioPharm International Supplements* 24(5):s27-s30). Thus, there remains a need for more uniform VLPs suitable vaccine development.

SUMMARY OF THE INVENTION

The disclosed subject matter of the present invention relates to novel virus-like particles (VLPs) having a matrix protein derived from an enveloped virus and a surface polypeptide and their uses. These VLPs are enveloped, and substantially uniform in size.

According to one aspect of the present invention, a virus-like particle (VLP) is provided. The VLP comprises a matrix protein derived from a first plant enveloped virus and a surface polypeptide. The surface polypeptide comprises a surface exposed portion derived from a target polypeptide, a transmembrane domain, and a cytosolic tail. The cytosolic tail is derived from a transmembrane protein (e.g., glycoprotein) of a second plant enveloped virus. The VLP may be produced in a plant cell, a plant, or a portion of a plant.

The first and the second plant enveloped viruses may be the same or different, preferably the same. Either may be a plant rhabdovirus or non-rhabdovirus. Preferably, the first plant enveloped virus is a plant rhabdovirus. The plant rhabdovirus may be selected from the group consisting of Lettuce Necrotic Yellows virus (LNYV), Northern Cereal Mosaic virus (NCMV), Sonhus Virus (SonV) and Broccoli necrotic yellows virus (BNYV). Preferably, the plant rhabdovirus is Lettuce Necrotic Yellows virus (LNYV).

The surface exposed portion of the surface polypeptide may be an antigenic polypeptide, such as a vaccine component, or may be a therapeutic agent. The therapeutic agent may be a therapeutic polypeptide.

The target polypeptide may be derived from a pathogen. The pathogen may be selected from the group consisting of a virus, a bacterium, a parasite and a fungus. The virus may be an animal virus. The animal virus may be selected from the group consisting of an influenza virus, a respiratory syncytial virus (RSV), a human immunodeficiency virus (HIV), a hepatitis B virus (HBV), a hepatitis C virus (HCV), a human papillomavirus (HPV), an Ebola virus, a Yellow fever virus, a rotovirus, and a vesicular stomatitis virus (VSV).

The target polypeptide may be a native surface polypeptide. The native surface polypeptide may be a hemagglutinin of an influenza virus.

The target polypeptide may be an artificial surface polypeptide. The artificial surface polypeptide may be protective antigen 83 (PA83) from *Bacillus anthracis*, Pfs25 from *Plasmodium falciparum* or other soluble protein or peptide.

The influenza virus may be selected from the group consisting of an Influenza A virus and an Influenza B virus. The influenza virus may be selected from the group consisting of Influenza A Indonesia 05/05 strain, Influenza A virus California/04/2009 (H1N1) strain, Influenza A/Victoria/3/75 (H3N2) strain and Influenza B Hong Kong/330/2001.

The target polypeptide may be a therapeutic agent. The therapeutic agent may be a therapeutic polypeptide.

The transmembrane domain may be native or foreign to the surface exposed portion of the surface polypeptide. The transmembrane domain may be derived from a cellular or viral transmembrane protein. The viral transmembrane domain may be derived from the transmembrane protein from which the cytosolic tail is derived.

According to another aspect of the present invention, a method of producing virus-like particles (VLPs) in a plant cell, a plant, or a portion of a plant is provided. The method comprises introducing one or more nucleic acid molecules into the plant cell, the plant, or the portion of a plant. The one or more nucleic acid molecules comprise a first nucleotide sequence encoding a matrix protein derived from a first plant enveloped virus and a second nucleotide sequence encoding a surface polypeptide. The surface polypeptide comprises a surface exposed portion derived from a target polypeptide, a transmembrane domain, and a cytosolic tail. The cytosolic tail is derived from a transmembrane protein (e.g., glycoprotein) of a second plant enveloped virus. The first and second plant enveloped viruses may be the same or different, preferably the same. Either may be a plant rhabdovirus or non-rhabdovirus. Preferably, the first plant enveloped virus is a plant rhabdovirus. The method further comprises maintaining the plant cell, the plant, or the portion of a plant under conditions permitting co-expression of the matrix protein and the surface polypeptide such that the VLPs are produced. The VLPs may be substantially uniform in size. The method may further comprise purifying the VLPs from the plant cell, the plant or the portion of the plant.

The one or more nucleic acid molecules may be introduced into the plant cell, the plant or the portion of a plant by infiltration, particle bombardment, or inoculation. The one or more nucleic acid molecules may be introduced into the plant or a portion thereof transiently or stably.

Various immunogenic compositions are provided. In some embodiments, the immunogenic composition comprises an effective amount of the VLPs of the present invention, and the VLPs are substantially uniform in size. In other embodiments, the immunogenic composition comprises an effective amount of the VLPs produced by the method of the present invention, and the VLPs are substantially uniform in size. The immunogenic composition may further comprise an adjuvant and/or an excipient.

A method of inducing an immune response to the target polypeptide in a subject is provided. The method comprises administering to the subject an effective amount of the immunogenic composition of the present invention, wherein the VLPs are substantially uniform in size.

A method of inducing a protective immune response to a pathogen in a subject is also provided. The method comprises administering to the subject an effective amount of the immunogenic composition of the present invention, wherein the VLPs are substantially uniform in size. The target polypeptide is derived from the pathogen. The pathogen may be an influenza virus. The target polypeptide may be derived from a hemagglutinin.

A recombinant plant cell comprising one or more nucleic acid molecules is further provided. The one or more nucleic acid molecules comprise a first nucleotide sequence encoding a matrix protein derived from a first plant enveloped virus and a second nucleotide sequence encoding a surface polypeptide. The surface polypeptide comprises (a) a surface exposed portion derived from a target polypeptide, (b) a transmembrane domain, and (c) a cytosolic tail derived from a transmembrane protein (e.g., glycoprotein) of a second plant enveloped virus. The first and second plant enveloped viruses may be the same or different, preferably the same. Either may be a plant rhabdovirus or non-rhabdovirus. Preferably, the first plant enveloped virus is a plant rhabdovirus. Also provided is a plant or a portion thereof comprising the plant cell of the present invention.

BRIEF DESCRIPTION OF THE DRAWINGS

FIG. 3 is a diagram illustrating the genome organization of the T-DNA region of a miniBYV-HAi-TM/$M_{LNYV}$ or miniBYV-HAi-TM/$M_{NCMV}$ vector for co-expression of an HAi-TM protein and a matrix protein of Lettuce Necrotic Yellows virus (LNYV) ($M_{LNYV}$) or Northern Cereal Mosaic virus (NCMV) ($M_{NCMV}$), respectively. L-Pro, papain like leader proteinase; Met, Hel and Pol, methyltransferase, RNA helicase, RNA-dependent RNA polymerase domains of the replicase, respectively; 2Enx35S; 35S promoter with dual enhancers from Cauliflower mosaic virus; NOS—Nopaline synthase terminator; LB and RB, left and right borders of the T-DNA, respectively.

FIG. 4 is a diagram illustrating the genome organization of the T-DNA region of a miniBYV-HAi-TM(G)/$M_{LNYV}$ vector for co-expression of an HAi-TM(G)$_{LNYN}$ protein and an $M_{LNYV}$ protein. L-Pro, papain like leader proteinase; Met, Hel and Pol, methyltransferase, RNA helicase, RNA-dependent RNA polymerase domains of the replicase, respectively; 2Enx35S, 35S promoter with dual enhancers from Cauliflower mosaic virus; NOS—Nopaline synthase terminator; LB and RB, left and right borders of the T-DNA, respectively.

FIG. 11 shows the amino acid sequences of (A) a hemagglutinin of H5N1 avian influenza virus (A/Indonesia/05/2005) (HAi-TM) (SEQ ID NO: 1) having a PR1a *Nicotiana tabacum* signal peptide (underlined), an HAi ectodomain, an HAi transmembrane domain (bold), and an HAi cytosolic tail (italicized), and (B) a hemagglutinin of H5N1 avian influenza virus (A/Indonesia/05/2005) (HAi-TM(G)$_{LNYV}$) (SEQ ID NO: 2) having a PR1a *N. tabacum* signal peptide (underlined), an HAi ectodomain, a transmembrane domain of an LNYV glycoprotein (bold), and a cytosolic tail of an LNYV glycoprotein (italicized).

FIG. 12 shows the amino acid sequences of (A) a matrix protein of LNYV ($M_{LNYV}$) (SEQ ID NO: 3) and (B) a matrix protein of H5N1 avian influenza virus (A/Indonesia/05/2005) (M1 protein) (SEQ ID NO: 4).

DETAILED DESCRIPTION OF THE INVENTION

Figure 1:
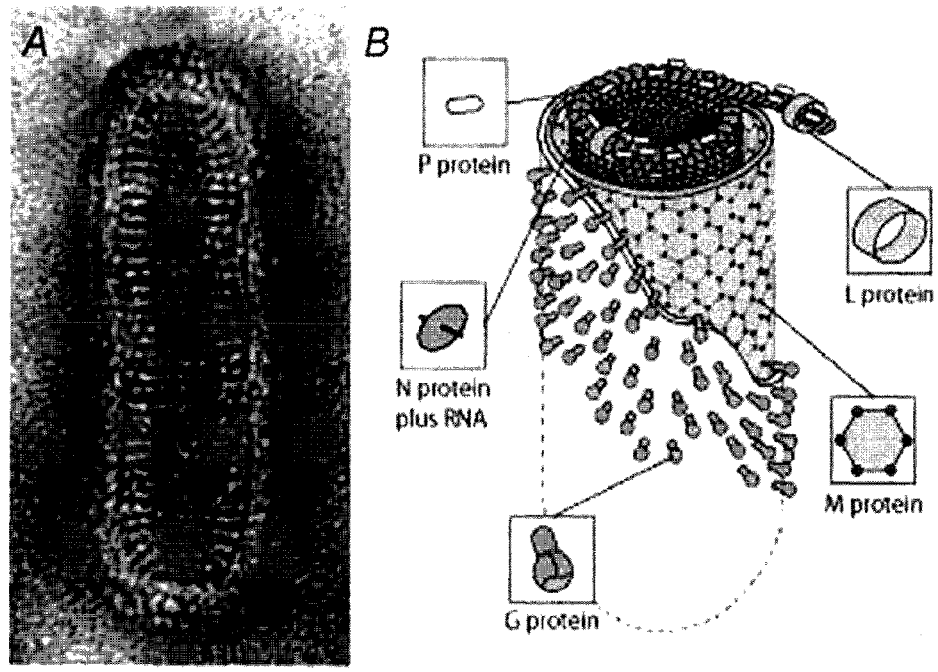
FIG. 1 shows (A) an electron microscopy image and (B) the organization of a plant rhabdovirus.

The present invention is based on the discovery that novel virus-like particles (VLPs) comprising a matrix protein derived from a plant enveloped virus and a surface polypeptide can be produced in plants. These VLPs are enveloped, and are substantially uniform in size, and may be used to design and manufacture effective human vaccines.

The term "protein" used herein refers to a biological molecule comprising amino acid residues. A protein may comprise one or more polypeptides. Each polypeptide may be a subunit of a protein. The protein may be in a native or modified form, and may exhibit a biological function when its polypeptide or polypeptides are properly folded or assembled.

The term "polypeptide" used herein refers to a polymer of amino acid residues with no limitation with respect to the minimum length of the polymer. Preferably, the polypeptide has at least 4 amino acids. A polypeptide may be a full-length protein, or a fragment or variant thereof.

The term "fragment" of a protein as used herein refers to a polypeptide having an amino acid sequence that is the same as a part, but not all, of the amino acid sequence of the protein. Preferably, a fragment is a functional fragment of a protein that retains the same function as the protein.

The term "variant" of a protein used herein refers to a polypeptide having an amino acid sequence that is the same as that of the protein except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein.

The term "derived from" used herein refers to an origin or source, and may include naturally occurring, recombinant, unpurified or purified molecules. The molecules of the present invention may be derived from viral or non-viral molecules. A protein or polypeptide derived from an original protein or polypeptide may comprise the original protein or polypeptide, in part or in whole, and may be a fragment or variant of the original protein or polypeptide.

The term "native" used herein refers to a molecule (e.g., a protein or polypeptide) that is naturally occurring. The term "artificial" used herein refers to a molecule (e.g., a protein or polypeptide) that is not naturally occurring, but synthesized artificially, for example, recombinantly or chemically.

According to one aspect of the present invention, a virus-like particle (VLP) is provided. The VLP comprises a matrix protein and a surface polypeptide. The matrix protein is derived from a first plant enveloped virus, preferably plant rhabdovirus, more preferably, lettuce necrotic yellows virus. The surface polypeptide comprises a surface exposed portion derived from a target polypeptide, a transmembrane domain and a cytosolic tail. The cytosolic tail is derived from a transmembrane protein (e.g., glycoprotein) of a second plant enveloped virus. For example, the cytosolic tail may be derived from a rhabdoviral glycoprotein. The transmembrane domain and the cytosolic tail may be derived from the same or different plant enveloped viruses, preferably from the same plant enveloped virus. In one embodiment, the transmembrane domain is derived from a target protein while the cytosolic tail is derived from a rhabdovirus glycoprotein. In another embodiment, the transmembrane domain and the cytosolic tail are both derived from the same plant rhabdoviral glycoprotein. The matrix protein, the transmembrane domain and the cytosolic tail may be derived from the same plant enveloped virus.

The VLP may be produced in a plant cell or other cells. The plant cell may be a cell in a plant, a plant part (e.g., leaf, stem, root, floral tissue, seed or petiole), or a cell culture medium. The plant may be a whole growing plant. Preferably, the plant cell is in a plant leaf. The cell culture media may be any media suitable for growing plant cells, preferably in suspension. The plant cell is preferably suitable for expression of a VLP. For example, the plant cell may be in *N. benthamiana* leaves. Other suitable plants include *Nicotiana clevelandii, Beta vulgaris, Spinacia oleracea, Brassica* spp, *Lactuca sativa, Pisum sativum, Nicotiana tabacum, Plantago lanceolata, Tetragonia tetragonioides, Montia perfoliata, Stellaria media, Medicago truncatula*, and *Chenopodium foliosum.*

The VLP may comprise a membrane. The surface polypeptide of the VLP may be integrated into the membrane. The membrane may be derived from the cell in which the VLP is assembled, made or produced.

The matrix protein may be derived from a natural matrix protein of any plant enveloped virus. The matrix protein may have an amino acid sequence at least about 80%, 85%, 90%, 95%, or 99%, preferably at least about 90%, more preferably at least about 95%, further preferably at least about 99%, most preferably about 100%, identical to that of the corresponding natural matrix protein.

The surface exposed portion derived from a target polypeptide is a portion of the surface polypeptide that is on the surface of the VLP. The surface polypeptide may be an antigenic polypeptide, such as a vaccine component, or may be a therapeutic agent. The therapeutic agent may be a therapeutic polypeptide. The surface polypeptide, either in the VLP or purified from the VLP, may be used for various purposes. For example, the surface polypeptide may be antigenic and used to induce an immune response in a subject when introduced into the subject. It may also be used as a therapeutic agent to treat a disease or disorder in a subject when administered to the subject. It may further be used as a diagnostic agent for diagnosis of a disease or disorder in a subject when used in testing a sample from the subject suspected of having the disease or disorder.

The surface polypeptide may be derived from an antigenic target polypeptide, and capable of inducing an immune response in a subject when introduced into the subject, and may be used to form or become a vaccine candidate. It may comprise one or more epitopes (linear and/or conformational) capable of stimulating the immune system of a subject to make a humoral and/or cellular antigen-specific immune response. A humoral immune response refers to an immune response mediated by antibodies produced by B lymphocytes, or B cells, while a cellular immune response refers to an immune response mediated by T lymphocytes, or T cells, and/or other white blood cells. In general, a B-cell epitope contains at least about 5 amino acids but can be 3-4 amino acids, while a T-cell epitope includes at least about 7-9 amino acids and a helper T-cell epitope includes at least 12-20 amino acids. The target polypeptide may be derived from, in part or in whole, a natural protein (e.g., a surface protein or toxin subunit) of a pathogenic organism or pathogen. The target polypeptide may comprise an amino acid sequence at least about 10%, 20%, 30%, 40%, 50%, 60%, 70%, 80%, 85%, 90%, 95%, or 99%, preferably at least about 90%, more preferably at least about 95%, further preferably at least about 99%, most preferably about 100%, identical to that of the corresponding natural pathogenic protein. The pathogen may be an intracellular or extracellular pathogen. Exemplary pathogens include viruses, bacteria, parasites and fungi. The viruses may be animal or plant viruses, preferably animal viruses. An animal virus may be selected from the group consisting of an influenza virus, a respiratory syncytial virus (RSV), a human immunodeficiency virus (HIV), a hepatitis B virus (HBV), a hepatitis C virus (HCV), a human papillomavirus (HPV), an Ebola virus, a Yellow fever virus, a rotovarus, and a vesicular stomatitis virus (VSV). Preferably, the target polypeptide is derived from an influenza virus.

The target polypeptide may be a native surface polypeptide or an artificial surface polypeptide. The native surface polypeptide may be a hemagglutinin of an influenza virus. The artificial surface polypeptide may be protective antigen 83 (PA83), Pfs25, or other soluble protein or peptide. The PA83 is from *Bacilus anthracis*. The Pfs25 is from *Plasmodium falciparum*.

An influenza virus may be selected from the group consisting of an Influenza A virus and an Influenza B virus. The influenza virus may be selected from the group consisting of Influenza A Indonesia 05/05 strain, Influenza A virus California/04/2009 (H1N1) strain, Influenza A/Victoria/3/75 (H3N2) strain and Influenza B Hong Kong/330/2001.

The transmembrane domain of the surface polypeptide may be a native protein or an artificial protein. The transmembrane domain may be native or foreign to the surface exposed portion of the surface polypeptide or the target polypeptide. The transmembrane domain may be derived from a transmembrane protein, preferably the same transmembrane protein, from which the matrix protein and the cytosolic tail are derived. The transmembrane domain may be derived from a cellular or viral transmembrane protein, or a surface protein. The transmembrane domain may or may not be derived from the target polypeptide. The viral transmembrane protein may be a transmembrane protein from a plant virus. The plant virus may be a plant enveloped virus, preferably the plant enveloped virus from which the matrix protein and the cytosolic tail are derived. The transmembrane domain may be derived from a glycoprotein of a virus, preferably a glycoprotein of a plant enveloped virus, more preferably a glycoprotein of the plant enveloped virus from which the matrix protein and the cytosolic tail are derived.

A plant enveloped virus has a lipid envelope. This lipid envelope is typically derived from the membrane of a host cell from which the virus particle buds off. The plant enveloped virus may be a plant rhabdovirus or non-rhabdovirus. Examples of plant rhabdoviruses include Lettuce Necrotic Yellows virus (LNYV), Northern Cereal Mosaic virus (NCMV), Sonhus Virus (SonV) Broccoli necrotic yellows virus (BNYV), and other plant rhabdoviruses recognized by the International Committee on Taxonomy of Viruses (ICTV). Preferably, the plant enveloped virus is Lettuce Necrotic Yellows virus (LNYV).

LNYV and NCMV rhabdoviruses are characterized by monocistronic negative sense RNA and belong to the family Rhabdoviridae and the genus Cytorhabdoviruses. Plant rhabdoviruses are characterized by the bacilli-form structure (FIG. 1A) and are about 130-350 nm in length and about 40-100 nm in width (Jackson et al, 2005, *Ann. Rev. Phytopathol*. 43:623-660). The two proteins of the virus that are key for assembly of bacilli-form particles are matrix protein (M protein) and glycoprotein (G protein). M protein forms a layer inside the virion's envelope and interacts with the cytosolic tale of G protein (FIG. 1B).

According to another aspect of the present invention, a method for producing the VLPs of the present invention in a plant cell, a plant, or a portion of a plant is provided. The method comprises introducing one or more nucleic acid molecules into the plant cell, the plant, or the portion of a plant. The one or more nucleic acid molecules comprise a first nucleotide sequence encoding the matrix protein and a second nucleotide sequence encoding the surface polypeptide. The matrix protein is derived from a first plant enveloped virus. The surface polypeptide comprises a surface exposed portion derived from a target polypeptide, a transmembrane domain, and a cytosolic tail. The cytosolic tail is derived from a transmembrane protein (e.g., glycoprotein) of a second plant enveloped virus. For example, the cytosolic tail may be derived from a plant rhabdoviral glycoprotein. The transmembrane domain may or may not be derived from the target polypeptide. The first and the second plant enveloped viruses may be the same or different, preferably the same. Either may be a plant rhabdovirus or non-rhabdovirus. Preferably, the first enveloped plant virus is a plant rhabdovirus. The method further comprises maintaining the plant cell, the plant, or the portion of a plant under conditions permitting co-expression of the matrix protein and the surface polypeptide such that the VLPs are produced.

The VLPs produced by a method according to the present invention may be of any sizes. For example, the VLPs may have a diameter in the range of about 5-350 nm, including about 40-60 nm. Preferably, the VLPs are substantially uniform in size. The term "substantially uniform in size" used herein means that at least about 50%, 60%, 70%, 80%, 90%, 95% or 99%, preferably at least about 80%, more preferably at least about 90%, most preferably at least about 95%, of the VLPs have a diameter within less than about 50%, 45%, 40%, 35%, 30%, 25%, 20%, 15%, 10%, or 5%, preferably less than about 30%, more preferably less than about 20%, most preferably less than 10%, of the average diameter of all the VLPs. The diameter of a VLP may be the average or mean value of one or more measurements of the diameter of the VLP. The diameter of a VLP may be determined by conventional techniques known in the art, for example, by observation using an electron microscopy, sucrose gradient fractionation, size exclusion chromatography, and dynamic light scattering. The diameter values of the VLPs may be analyzed using various software, for example, ImageJ software (NIH, Bethesda, Md.) and other commercially available software.

The one or more nucleic acid molecules may further comprise a regulatory region operatively linked to the first or second nucleotide sequence. The regulatory region may be activated in a plant cell for the expression of the protein encoded by the first or the second nucleotide sequence. The regulatory region may include a promoter, for example, a plant viral promoter. Preferably, the first and second nucleotide sequences are in the same nucleic acid molecule, but linked to separate regulatory regions. The one or more nucleic acid molecules may further comprise a third nucleotide sequence encoding an additional surface polypeptide.

For each nucleic acid molecule, a vector comprising the nucleotide sequence of the nucleic acid molecule is provided. The vector may include a border sequence of a bacterial transfer DNA at either end, situated in a bacterial transfer DNA, to allow for delivery of the nucleic acid into a plant cell. Specifically, the vector may comprise one or more nucleic acid sequences derived from a Ti plasmid of a binary vector, and may also comprise a plant viral sequence. Such a vector, including elements of a Ti plasmid and a viral vector, is also called a launch vector. This vector may also be used for co-expression of the protein or polypeptide of interest (e.g., the matrix protein and/or the surface polypeptide) with a protein such as a silencing suppressor or a post-translational modifying enzyme such as PNGaseF, to modify, affect expression and/or increase production of the protein of interest by, for example, facilitating maturation or accumulation of the protein.

Each nucleic acid molecule may be introduced into the plant cell, the plant, or the portion of a plant (e.g., leaf, stem, root, floral tissue, seed or petiole) using techniques known in the art. For example, the nucleic acid molecule may be delivered via infiltration, particle bombardment, or inoculation. The nucleic acid molecule could be used as a part of an inducible system activated by, for example, chemical, light or heat shock. Preferably, the nucleic acid molecule is introduced into the plant cell via infiltration. The nucleic acid molecule may be introduced transiently or stably.

A recombinant plant cell comprising one or more nucleic acid molecules is provided. The one or more nucleic acid molecules comprise a first nucleotide sequence encoding a matrix protein and a second nucleotide sequence encoding a surface polypeptide. Preferably, the first and second nucleotide sequences are in one nucleic acid molecule. The matrix protein is derived from a first plant enveloped virus. The surface polypeptide comprises a surface exposed portion derived from a target polypeptide, a transmembrane domain and a cytosolic tail. The cytosolic tail is derived from a transmembrane protein (e.g., glycoprotein) of a second plant enveloped virus. The first and second plant enveloped viruses may be the same or different, preferably the same. Either may be a plant rhabdovirus or non-rhabdovirus. Preferably, the first plant enveloped virus is a plant rhabdovirus. The transmembrane domain may or may not be derived from the target polypeptide. The cytosolic tail may be derived from a glycoprotein of a plant enveloped virus. For example, the cytosolic tail may be derived from a rhabdoviral glycoprotein. The first or second nucleotide sequence may be operatively linked to a promoter capable of being activated in the plant cell for co-expression of the matrix protein or the surface polypeptide, respectively. Also provided is a plant or a portion thereof comprising the plant cell of the present invention.

For production of the VLPs of the present invention, a plant cell, or a plant or a portion thereof may be maintained under conditions permitting co-expression of the matrix protein and the surface polypeptide, resulting in the production of the VLPs. Such conditions include suitable temperature, humidity, pressure, light/dark cycle, and illumination. Preferably, the matrix protein and the surface polypeptide are co-expressed in the same plant cells.

The production method may further comprise purifying the VLPs. Conventional purification techniques known in the art may be used. For example, the VLP may be purified from the plant cell using an antibody or a receptor capable of binding the surface polypeptide. The purification process may comprise extraction of the VLPs from the plant cell using an extraction buffer. After low speed centrifugation, supernatant may be clarified by filtration and used for chromatography. The purified VLPs may be at least about 10%, 20%, 30%, 40%, 50%, 60%, 70%, 80%, 90%, 95% or 99%, preferably at least about 50%, more preferably at least about 75%, most preferably at least about 95%, pure. The VLPs in a crude plant extract may be used.

An immunogenic composition is provided. The composition comprises an effective amount of the VLPs of the present invention. Preferably, the VLPs are substantially uniform in size. The effective amount of the VLPs is an amount of the VLPs sufficient to make the composition immunogenic, i.e., capable of inducing an immune response in a subject when introduced into the subject. The composition may further comprise an adjuvant and/or an excipient. The immunogenic compositions may be used to induce an immune response in a subject. Several methods of inducing an immune response are provided.

A method of inducing an immune response to the target polypeptide in a subject is provided. The method comprises administering to the subject an effective amount of the immunogenic composition of the present invention. Preferably, the VLPs are substantially uniform in size. The immunogenic composition may be administered in an appropriate number of doses.

A method of inducing a protective immune response to a pathogen in a subject is also provided. The method comprises administering to the subject an effective amount of the immunogenic composition of the present invention. Preferably, the VLPs are substantially uniform in size. The target polypeptide is derived from the pathogen. For example, the target polypeptide may be a hemagglutinin and the pathogen is an influenza virus.

The subject may be an animal, including a mammal, for example, a human, a mouse, a cow, a horse, a chicken, a dog, a cat, and a rabbit. The animal may be an agricultural animal (e.g., horse, cow and chicken) or a pet (e.g., dog and cat). The subject is preferably a human or a mouse, more preferably a human. The subject may be a male or female. The subject may also be a newborn, a child or an adult. The subject may have suffered or be predisposed to a disease or medical condition, which may be caused by or associated with a pathogen.

The immunogenic composition may be formulated, for example, for oral, sublingual, intranasal, intraocular, rectal, transdermal, mucosal, topical or parenteral administration. Parenteral administration may include intradermal, subcutaneous (s.c., s.q., sub-Q, Hypo), intranasal, intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids) administration. Any device suitable for parenteral injection or infusion of the composition may be used for such administration.

The term "an effective amount" refers to an amount sufficient to achieve a stated goal, and may vary depending on the stated goal and other factors. For example, an effective amount of VLPs in an immunogenic composition or an effective amount of an immunogenic composition comprising VLPs may vary depending on the physical characteristics of the subject, the nature and severity of the need of the VLPs, the existence of related or unrelated medical conditions, the nature of the VLPs, the means of administering the VLPs to the subject, and the administration route. A specific dose for a given subject may generally be set by the judgment of a physician. The immunogenic composition may be administered to the subject in one or multiple doses.

Various medicaments comprising the VLPs of the present invention are provided. The VLPs are preferably substantially uniform in size. The medicaments may comprise suitable adjuvants. In some embodiments, the medicaments are useful for inducing an immune response to the target polypeptide in a subject, and comprise an effective amount of the VLPs of the present invention. In some other embodiments, the medicaments are useful for inducing a protective immune response to a pathogen in a subject, and comprise an effective amount of the VLPs of the present invention, wherein the target polypeptide is derived from the pathogen. For example, the target polypeptide may be a hemagglutinin and the pathogen is an influenza virus.

For each medicament of the present invention, a method for preparing the medicament is provided. The preparation method comprises admixing the VLPs of the present invention with a pharmaceutically acceptable carrier and/or excipient. The VLPs are preferably substantially uniform in size.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1

Construction of Mini-BYV Vectors

Figure 2:
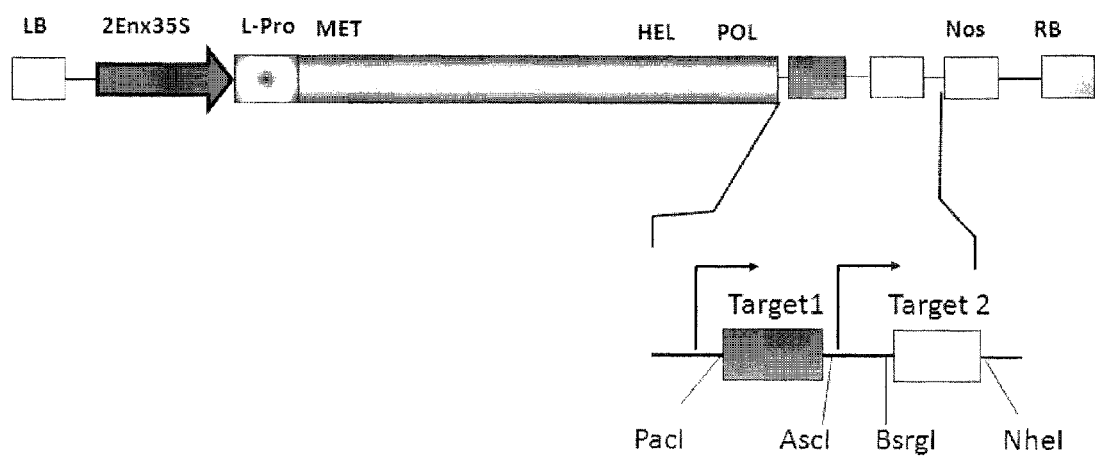
FIG. 2 is a diagram illustrating the genome organization of the T-DNA region of a miniBYV vector for co-expression of two target proteins, i.e., Target 1 and Target 2, each operatively linked to a regulatory region. L-Pro, papain like leader proteinase; Met, Hel and Pol, methyltransferase, RNA helicase, RNA-dependent RNA polymerase domains of the replicase, respectively; 2Enx35S, 35S promoter with dual enhancers from Cauliflower mosaic virus; NOS—Nopaline synthase terminator; LB and RB, left and right borders of the T-DNA, respectively.

To demonstrate the feasibility of assembling VLPs using matrix proteins (M proteins) from different plant enveloped viruses, a rhabdoviral M protein and a target antigen containing a transmembrane (TM) domain and a cytosolic tail of a LNYV glycoprotein (G protein) were engineered for co-expression in plant cells. For co-expression of these proteins, a miniBYV vector was used (FIG. 2). The miniBYV vector contains a minireplicon derived from a Closteroveridae virus (e.g., Beet yellows virus), which comprises a nucleic acid sequence encoding only proteins required for replication of the Closteroveridae virus. Specifically, the M protein from LNYV or NCMV was co-expressed with a hemagglutinin (HAi) from H5N1 avian influenza virus (A/Indonesia/05/2005).

In brief, a gene encoding a HAi protein having its native TM domain (HAi-TM) was cloned into a miniBYV vector to generate the miniBYV-HAi-TM plasmid. The HAi-TM protein (SEQ ID NO: 1) included a PR1a Nicotiana tabacum signal peptide (underlined), an HAi ectodomain, an HAi native transmembrane domain (bold), and an HAi native cytosolic tail (italicized) (FIG. 11A). Subsequently, a gene encoding the M protein of LNYV ($M_{LNYV}$ protein) or NCMV ($M_{NCMV}$ protein) was introduced into the miniBYV-HAi-TM plasmid under the control of the closteroviral heterologous coat protein (CP) promoter to generate a miniBYV-Hai-TM/$M_{LNYV}$ or miniBYV-Hai-TM/$M_{NCMV}$ plasmid (FIG. 3). For VLP evaluation, positive clones were transformed into Agrobacterium tumefaciens strain GV3101 and then introduced into Nicotiana benthamiana plants to produce VLPs.

In parallel, the HAi gene was modified to encode a recombinant a hemagglutinin protein (HAi-TM(G)), in which the native TM and the cytosolic tail of HAi were replaced with the transmembrane domain and cytosolic tail from a glycoprotein of LNYV, respectively. A nucleotide sequence encoding the HAi-TM(G) protein (SEQ ID NO: 2), including a PR1a Nicotiana tabacum signal peptide (underlined), an HAi ectodomain, an LNYV glycoprotein transmembrane domain (bold), and an LNYV glycoprotein cytosolic tail (italicized) (FIG. 11B), was introduced into the miniBYV vector containing a nucleotide sequence encoding the M protein of LNYV ($M_{LNYV}$ protein) (SEQ ID NO: 3) (FIG. 12A). The resulting construct, miniBYV-HAi-TM(G)/$M_{LNYV}$ (FIG. 4), was sequenced, and positive clones were transformed into A. tumefaciens and then introduced into Nicotiana benthamiana plants to produce HAi-TM(G)-$M_{LNYV}$ VLPs.

As a control, a gene encoding the matrix protein (M1 protein) of H5N1 avian influenza virus (A/Indonesia/05/2005) (SEQ ID NO: 4) (FIG. 12B) was introduced into the minBYV-HAi-TM plasmid under the control of the closteroviral heterologous coat protein (CP) promoter to generate the plasmid miniBYV-HAi-TM/M1. As described above, PR1a was used as a signal peptide. Positive clones were transformed into A. tumefaciens and then introduced into Nicotiana benthamiana plants to produce HAi-TM/M1 VLPs.

Example 2

Optimization of Infiltration Procedure to Express Hai

To evaluate the expression level of HAi and develop vacuum infiltration conditions, hydroponically grown N. benthamiana plants were used. To analyze the expression of HAi-TM, manual infiltration and vacuum infiltration of miniBYV-HAi-TM were performed using the same buffer. Five week old Nicotiana benthamiana plants grown in Rockwool in clam shells were used for vacuum and manual infiltration. Agrobacteria were grown in LB media, which was supplemented with 50 ng/ml Kanamycin and 50 ng/ml Hygromycin. One liter overnight cultures were grown at 28° C., shaking at 220 rpm for 18-24 hours.

Overnight concentration was determined by measuring the $OD_{600}$ for each culture. The agrobacteria were pelleted by spinning at 4000 g for 15 min at 4° C. Bacterial pellets were re-suspended in 100 ml of fresh MMA media (10 mM MgCl2; 10 mM MES, pH 5.85; and 20 µM acetosyringone). The final concentration for each culture was recorded after rocking for 2 hours at room temperature. Cultures containing miniBYV and P1/HcPro silencing suppressor (miniBYV requires use of a silencing suppressor to achieve good target expression levels) were mixed to ratios of $OD_{600}$, 1.0:0.2, respectively. For vacuum infiltration, clamshells were infiltrated with miniBYV:P1/HcPro containing agrobacteria. Infiltrated plants were fed 50 ppm hydrosol and placed in a growth room for 5-8 days.

For manual infiltration, 3-5 leaves of hydroponically grown Nicotiana benthamiana were manually infiltrated using a 10 cc syringe without a needle. Plants were fed with 50 ppm hydrosol and kept in the post infiltration room for 5-8 days.

Figure 5:
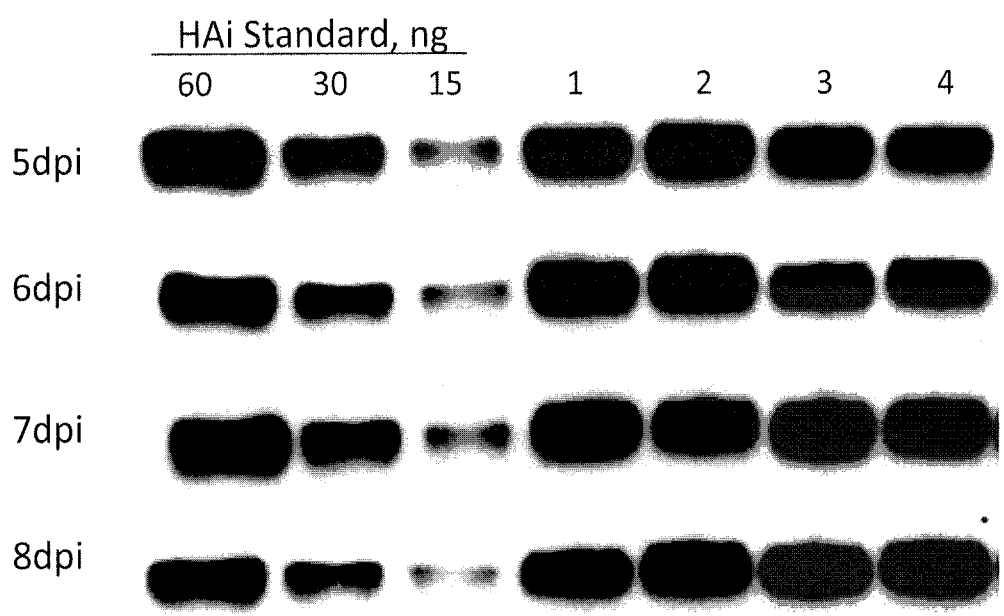
FIG. 5 depicts a representative western blot for time course analysis of HAi-TM expression detected by an anti-HAi 5G6 primary monoclonal antibody after infiltration. Reference HAi in the amount of 60, 30, or 15 ng was used as standard for quantification. Lanes 1 and 2, manual infiltrated *N. benthamiana;* 3 and 4, vacuum infiltrated *N. benthamiana*.

HAi-TM expression levels were determined based on the amount of HAi-TM protein detected by an anti-HAi 5G6 monoclonal antibody in Western blot analysis (FIG. 5). HAi-TM expression was higher in vacuum infiltrated leaves at 6 days post infiltrations (dpi) and 7 dpi compared to manually infiltrated leaves (Table 1). For example, at 6 dpi, the HAi-TM protein was expressed at 249 mg/kg in vacuum infiltrated leaves, representing a 43% increase in expression compared to manually infiltrated leaves.

TABLE 1

Time course expresssion levels for HAi-TM

| Days Post Infiltration | Manual Infiltration (mg/kg) | Vacuum Infiltration (mg/kg) |
| --- | --- | --- |
| 5 | 73 | 46 |
| 6 | 174 | 249 |
| 7 | 120 | 123 |
| 8 | 180 | 105 |

Example 3

Plant-Produced HAi-TM VLPs

Figure 6:
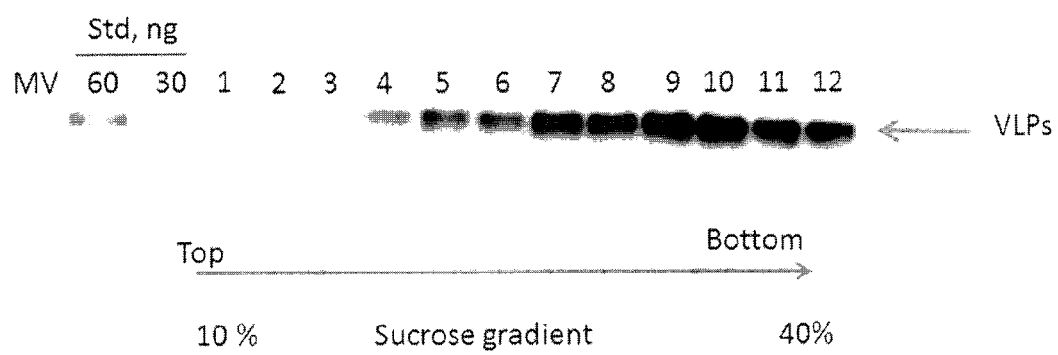
FIG. 6 shows (A) distribution of HAi-TM VLPs through a 10%-40% sucrose gradient and (B) morphology of the HAi-TM VLPs from fraction 10 of (A) detected by transmission electron microscopy (TEM) negative staining.
Figure 6:
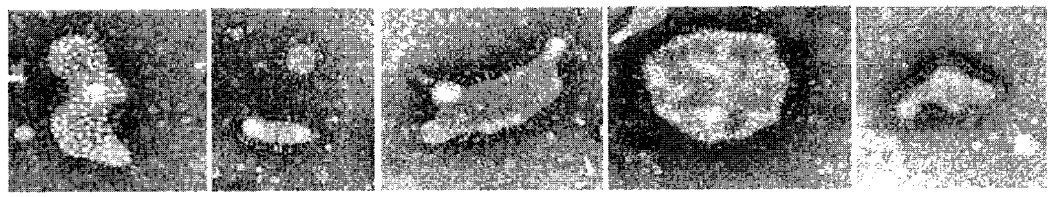

To characterize VLPs formation HAi-TM were cloned in to miniBYV vector using PacI/NheI restriction sites. The resulting plasmid miniBYV HAi-TM was transformed in to GV3101 Agrobacterium strain. Nicothiana benthamiana infiltrated leaves were harvested at 7 days post infiltration and VLPs were purified. Distribution of HAi-TM VLPs without any matrix protein through a 10%-40% sucrose gradient with peak fractions 9 and 10 was detected by an anti-HAi 5G6 mouse monoclonal antibody (developed by the Immunology group at Fraunhofer—USA Center for Molecular Biotechnology) (FIG. 6A). To evaluate the morphology of HAi-VLPs in fraction 10, VLPs from this fraction were analyzed by negative staining using transmission electron microscopy (TEM). HAi-TM VLPs with different sizes and shapes were observed (FIG. 6B).

Figure 7:
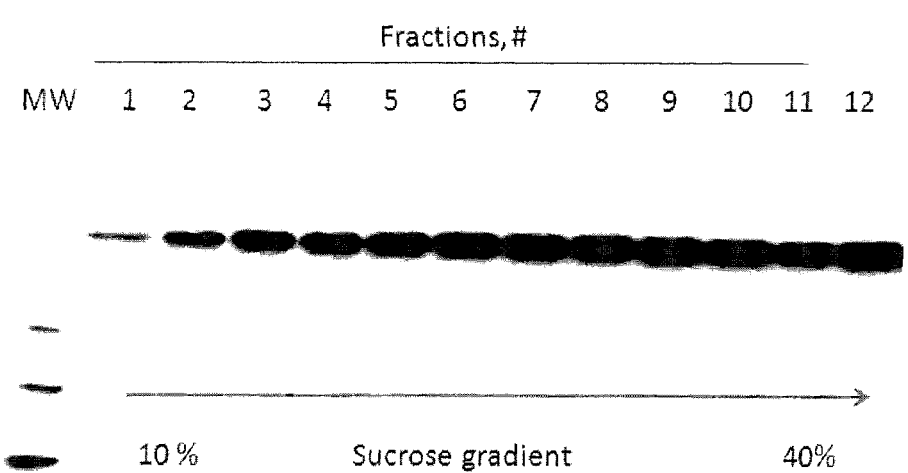
FIG. 7 shows (A) distribution of HAi-TM/M1 VLPs through a 10-40% sucrose gradient; and (B) morphology of the HAi-TM/M1 VLPs from fraction 10 of (A) detected by TEM negative staining.
Figure 7:
Figure 8:
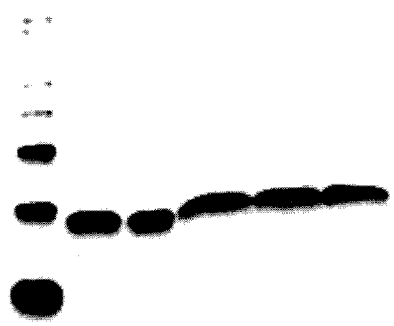
FIG. 8 shows (A) expression of the influenza A/Indonesia/05/2005 matrix (M1) protein in leaf samples (lanes 1-3, different replicas from the infiltrated plants producing HAi-TM/M1 VLPs); and (B) absence of the M1 protein from the HAi-TM/M1 VLPs in the 10-40% sucrose gradient fractions as shown on FIG. 7A. Std, M1 protein standard.
Figure 8:
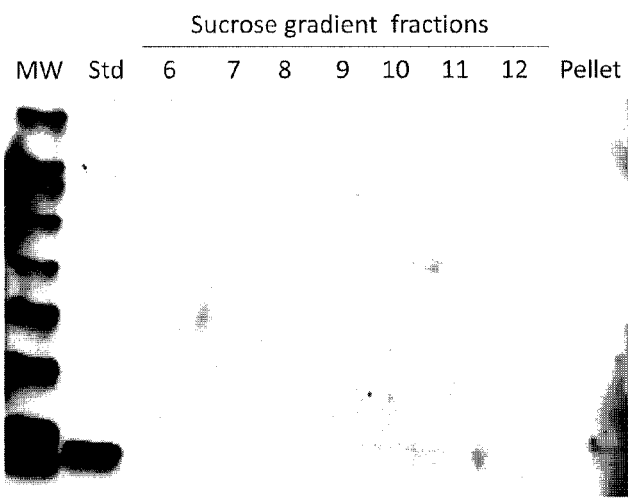

HAi-TM/M1 VLPs having HAi protein with its native transmembrane domain and cytosolic tail coexpressed with M1 of influenza A/Indonesia/05/05 were produced by expressing miniBYV-HAi-TM/M1 in plants using vacuum infiltration as described in Example 2. HAi-TM/M1 VLPs were purified using a sucrose gradient, and characterized by Western blot analysis and electron microscopy using the anti-HAi 5G6 mouse monoclonal antibody, and were found to distribute through a 10%-40% sucrose gradient with peak fractions 9 and 10 (FIG. 7A). No M1 protein incorporation was detected in the same HAi-TM/M1 VLPs through the 10-40% sucrose gradient (FIG. 8A) using a polyclonal goat anti-M1 antibody from Meredian Life science, Inc, USA. Meanwhile, the expression of M1 protein was confirmed by western blot using a goat anti-M1 protein polyclonal antibody (FIG. 8B). No uniformed VLPs were detected after co-expression HAi-TM and Influenza matrix M1 protein (FIG. 7B).

Example 4

Plant-Produced HAi-TM/$M_{LNYV}$ VLPs

Figure 9:
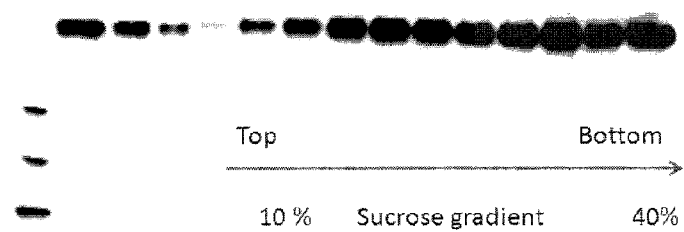
FIG. 9 shows (A) distribution HAi-TM/$M_{LNYV}$ VLPs in a 10-40% sucrose gradient and (B) immunogold labeling of the HAi-TM/$M_{LNYV}$ VLPs with an anti-HAi 5G6 mouse monoclonal antibody.
Figure 9:
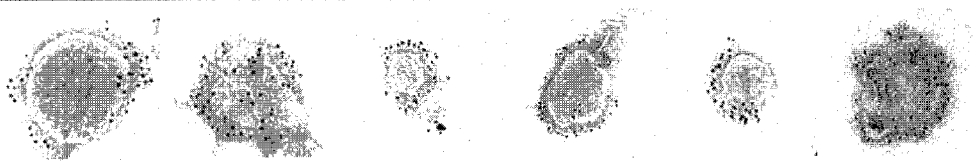

HAi-TM/$M_{LNYV}$ VLPs having HAi-TM protein (i.e., HAi protein with its native transmembrane domain and cytosolic tail) and LNYV M protein ($M_{LNYV}$ protein) were produced by expressing miniBYV-HAi-TM/$M_{LNYV}$ in plants using vacuum infiltration as described in Example 2. HAi-TM/$M_{LNYV}$ VLPs were purified using a 10%-40% sucrose gradient and characterized by SDS-PAGE, Western blot analysis and electron microscopy. The presence of the HAi immunological determinant on the surface of these VLPs was confirmed by immunogold labeling using the anti-HAi 5G6 mouse monoclonal antibody (FIG. 9B). Also, this antibody was used to detect VLPs distribution in a 10-40% sucrose gradient with a peak in fraction 10 (FIG. 9A). The distribution of HAi-TM/$M_{LNYV}$ VLPs was similar to that observed for HAi-TM/M1 VLPs (FIGS. 7A and 9A). There was no noticeable difference in the VLP morphology (e.g., shape and size) (FIGS. 7B and 9B).

Example 5

Plant-Produced Uniform HAi-TM(G)/$M_{LNYV}$ VLPs

Figure 10:
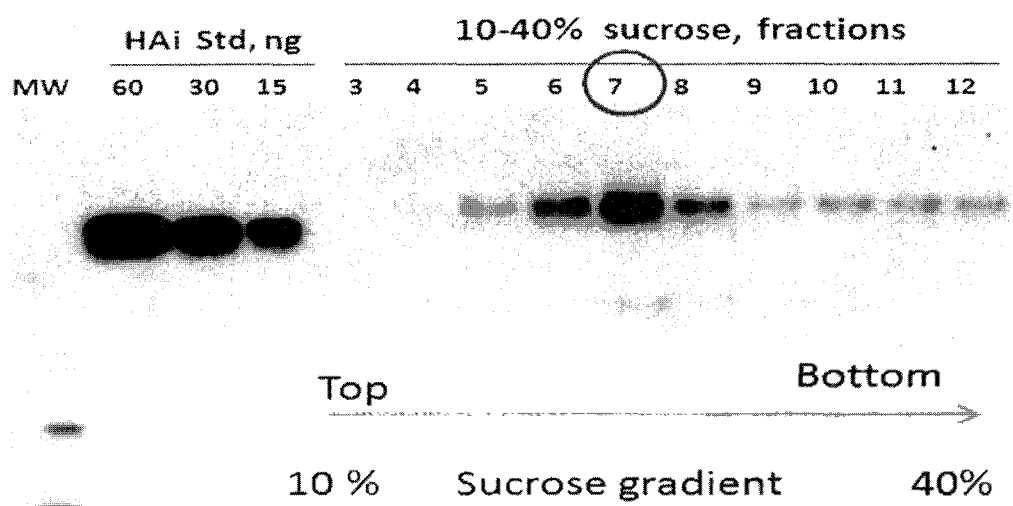
FIG. 10 shows (A) distribution of HAi-TM(G)/$M_{LNYV}$ VLPs through a 10%-40% sucrose gradient and (B) immunogold labeling of the HAi-TM(G)-$M_{LNYV}$ VLPs from fraction 7 of (A) with an anti-HAi 5G6 mouse monoclonal antibody.
Figure 10:
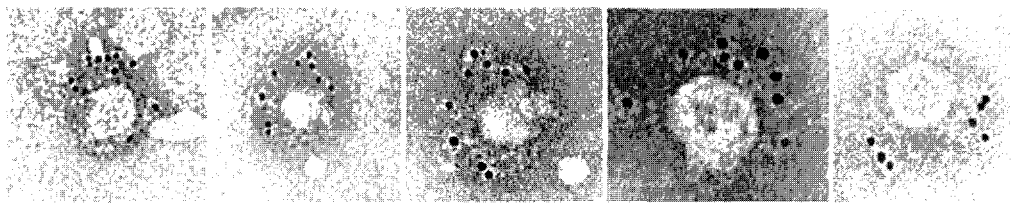

HAi-TM(G)/$M_{LNYV}$ VLPs having HAi-TM(G) protein (i.e., HAi protein with a transmembrane domain and a cytosolic tail from a rhabdoviral glycoprotein (G) protein) and LNYV M protein ($M_{LNYV}$ protein) were produced by expressing miniBYV-HAi-TM(G)/$M_{LNYV}$ in plants using vacuum infiltration as described in Example 2. After separation of HAi-TM(G)/$M_{LNYV}$ VLPs by a 10%-40% sucrose gradient, 1 mL fractions were collected and analyzed by Western blot analysis using the anti-HAi 5G6 monoclonal antibody. A shift in the target collection peak was observed. Unlike HAi-TM/$M_{LNYV}$ VLPs, the HAi-TM(G)/$M_{LNYV}$ VLPs were detected in fractions 6, 7 and 8 with a sharp peak in fraction 7 (FIG. 10A). Immunogold labeling following TEM showed round-shaped HAi-TM(G)/$M_{LNYV}$ VLPs (FIG. 10B). The size of the HAi-TM(G)/$M_{LNYV}$ VLPs determined by ImageJ software (NIH, Bethesda, Md.) was 50.5±15 nm. The HAi-TM(G)-$M_{LNYV}$ VLPs were substantially uniform in size and shape.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A virus-like particle comprising a matrix protein from a first plant enveloped virus and a surface polypeptide, wherein the first plant enveloped virus is a plant rhabdovirus, and wherein the surface polypeptide comprises
   (a) a surface exposed portion from a target polypeptide wherein the target polypeptide is a polypeptide not from the first plant enveloped virus,
   (b) a transmembrane domain, and
   (c) a cytosolic tail from a transmembrane protein of a second plant enveloped virus.

2. The virus-like particle of claim 1, wherein the first plant enveloped virus and the second plant enveloped virus are the same.

3. The virus-like particle of claim 1, wherein the virus-like particle is produced in a plant cell, a plant, or a portion of a plant.

4. The virus-like particle of claim 1, wherein the plant rhabdovirus is selected from the group consisting of Lettuce Necrotic Yellows virus (LNYV), Northern Cereal Mosaic virus (NCMV), Sonhus Virus (SonV), and Broccoli necrotic yellows virus (BNYV).

5. The virus-like particle of claim 1, wherein the surface exposed portion of the surface polypeptide is antigenic.

6. The virus-like particle of claim 1, wherein the target polypeptide is from a pathogen.

7. The virus-like particle of claim 1, wherein the surface exposed portion of the surface polypeptide is therapeutic.

8. The virus-like particle of claim 1, wherein the target polypeptide is a native polypeptide.

9. The virus-like particle of claim 1, wherein the target polypeptide is an artificial polypeptide.

10. The virus-like particle of claim 1, wherein the transmembrane domain is native or foreign to the surface exposed portion.

11. The virus-like particle of claim 1, wherein the transmembrane domain is from the transmembrane protein.

12. The virus-like particle of claim 1, wherein the transmembrane domain is from a cellular or viral transmembrane protein.

13. A method of producing virus-like particles of claim 1 in a plant cell, a plant or a portion of a plant, comprising
    (a) introducing one or more nucleic acid molecules into the plant cell, the plant or the portion of a plant, wherein the one or more nucleic acid molecules comprise a first nucleotide sequence encoding a matrix protein and a second nucleotide sequence encoding a surface polypeptide and wherein the surface polypeptide comprises
    (i) a surface exposed portion from a target polypeptide, wherein the target polypeptide is a polypeptide not from the first plant enveloped virus,
    (ii) a transmembrane domain, and
    (iii) a cytosolic tail from a transmembrane protein of a second plant enveloped virus; and
    (b) maintaining the plant cell, the plant or the portion of a plant under conditions permitting co-expression of the matrix protein and the surface polypeptide, whereby the virus-like particles are produced.

14. The method of claim 13, wherein the first plant enveloped virus and the second plant enveloped virus are the same.

15. The method of claim 13, wherein the virus-like particles are substantially uniform in size.

16. The method of claim 13, further comprising (c) purifying the virus-like particles.

17. The method of claim 13, wherein the one or more nucleic acid molecules are introduced into the plant cell, the plant or the portion of a plant by infiltration, particle bombardment, or inoculation.

18. The method of claim 13, wherein the one or more nucleic acid molecules are introduced into the plant cell, the plant or the portion of a plant transiently or stably.

19. An immunogenic composition comprising an effective amount of the virus-like particles of claim 1, wherein the virus-like particles are substantially uniform in size.

20. An immunogenic composition comprising an effective amount of the virus-like particles produced by the method of claim 13, wherein the virus-like particles are substantially uniform in size.

21. The immunogenic composition of claim 19, further comprising an adjuvant or an excipient.

22. A method of inducing an immunological response to a pathogen in a subject, comprising administering to the subject an effective amount of the virus like particles produced by the method of claim 13, wherein the target polypeptide is from the pathogen, and wherein the virus-like particles are substantially uniform in size.

* * * * *

SEQUENCE LISTING

<160> NUMBER OF SEQ ID NOS: 4

<210> SEQ ID NO 1
<211> LENGTH: 581
<212> TYPE: PRT
<213> ORGANISM: Avian influenza virus

<400> SEQUENCE: 1

```
Met Gly Phe Val Leu Phe Ser Gln Leu Pro Ser Phe Leu Leu Val Ser
1               5                   10                  15

Thr Leu Leu Phe Leu Val Ile Ser His Ser Cys Arg Ala Asp Gln
            20                  25                  30

Ile Cys Ile Gly Tyr His Ala Asn Asn Ser Thr Glu Gln Val Asp Thr
        35                  40                  45

Ile Met Glu Lys Asn Val Thr Val Thr His Ala Gln Asp Ile Leu Glu
    50                  55                  60

Lys Thr His Asn Gly Lys Leu Cys Asp Leu Asp Gly Val Lys Pro Leu
65                  70                  75                  80

Ile Leu Arg Asp Cys Ser Val Ala Gly Trp Leu Leu Gly Asn Pro Met
                85                  90                  95

Cys Asp Glu Phe Ile Asn Val Pro Glu Trp Ser Tyr Ile Val Glu Lys
            100                 105                 110

Ala Asn Pro Thr Asn Asp Leu Cys Tyr Pro Gly Ser Phe Asn Asp Tyr
```

```
            115                 120                 125
Glu Glu Leu Lys His Leu Leu Ser Arg Ile Asn His Phe Glu Lys Ile
130                 135                 140

Leu Ile Ile Pro Lys Ser Ser Trp Ser Asp His Glu Ala Ser Ser Gly
145                 150                 155                 160

Val Ser Ser Ala Cys Pro Tyr Leu Gly Ser Pro Ser Phe Phe Arg Asn
                165                 170                 175

Val Val Trp Leu Ile Lys Lys Asn Ser Thr Tyr Pro Thr Ile Lys Lys
            180                 185                 190

Ser Tyr Asn Asn Thr Asn Gln Glu Asp Leu Leu Val Leu Trp Gly Ile
        195                 200                 205

His Pro Asn Asp Ala Ala Glu Gln Thr Arg Leu Tyr Gln Asn Pro Thr
    210                 215                 220

Thr Tyr Ile Ser Ile Gly Thr Ser Thr Leu Asn Gln Arg Leu Val Pro
225                 230                 235                 240

Lys Ile Ala Thr Arg Ser Lys Val Asn Gly Gln Ser Gly Arg Met Glu
                245                 250                 255

Phe Phe Trp Thr Ile Leu Lys Pro Asn Asp Ala Ile Asn Phe Glu Ser
            260                 265                 270

Asn Gly Asn Phe Ile Ala Pro Glu Tyr Ala Tyr Lys Ile Val Lys Lys
        275                 280                 285

Gly Asp Ser Ala Ile Met Lys Ser Glu Leu Glu Tyr Gly Asn Cys Asn
    290                 295                 300

Thr Lys Cys Gln Thr Pro Met Gly Ala Ile Asn Ser Ser Met Pro Phe
305                 310                 315                 320

His Asn Ile His Pro Leu Thr Ile Gly Glu Cys Pro Lys Tyr Val Lys
                325                 330                 335

Ser Asn Arg Leu Val Leu Ala Thr Gly Leu Arg Asn Ser Pro Gln Arg
            340                 345                 350

Glu Ser Arg Arg Lys Lys Arg Gly Leu Phe Gly Ala Ile Ala Gly Phe
        355                 360                 365

Ile Glu Gly Gly Trp Gln Gly Met Val Asp Gly Trp Tyr Gly Tyr His
    370                 375                 380

His Ser Asn Glu Gln Gly Ser Gly Tyr Ala Ala Asp Lys Glu Ser Thr
385                 390                 395                 400

Gln Lys Ala Ile Asp Gly Val Thr Asn Lys Val Asn Ser Ile Ile Asp
                405                 410                 415

Lys Met Asn Thr Gln Phe Glu Ala Val Gly Arg Glu Phe Asn Asn Leu
            420                 425                 430

Glu Arg Arg Ile Glu Asn Leu Asn Lys Lys Met Glu Asp Gly Phe Leu
        435                 440                 445

Asp Val Trp Thr Tyr Asn Ala Glu Leu Leu Val Leu Met Glu Asn Glu
    450                 455                 460

Arg Thr Leu Asp Phe His Asp Ser Asn Val Lys Asn Leu Tyr Asp Lys
465                 470                 475                 480

Val Arg Leu Gln Leu Arg Asp Asn Ala Lys Glu Leu Gly Asn Gly Cys
                485                 490                 495

Phe Glu Phe Tyr His Lys Cys Asp Asn Glu Cys Met Glu Ser Ile Arg
            500                 505                 510

Asn Gly Thr Tyr Asn Tyr Pro Gln Tyr Ser Glu Glu Ala Arg Leu Lys
        515                 520                 525

Arg Glu Glu Ile Ser Gly Val Lys Leu Glu Ser Ile Gly Thr Tyr Gln
    530                 535                 540
```

```
Ile Leu Ser Ile Tyr Ser Thr Val Ala Ser Leu Ala Leu Ala Ile
545                 550                 555                 560

Met Met Ala Gly Leu Ser Leu Trp Met Cys Ser Asn Gly Ser Leu Gln
            565                 570                 575

Cys Arg Ile Cys Ile
            580

<210> SEQ ID NO 2
<211> LENGTH: 594
<212> TYPE: PRT
<213> ORGANISM: Avian influenza virus

<400> SEQUENCE: 2

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Asp Gln
                20                  25                  30

Ile Cys Ile Gly Tyr His Ala Asn Asn Ser Thr Glu Gln Val Asp Thr
            35                  40                  45

Ile Met Glu Lys Asn Val Thr Val Thr His Ala Gln Asp Ile Leu Glu
50                  55                  60

Lys Thr His Asn Gly Lys Leu Cys Asp Leu Asp Gly Val Lys Pro Leu
65                  70                  75                  80

Ile Leu Arg Asp Cys Ser Val Ala Gly Trp Leu Leu Gly Asn Pro Met
                85                  90                  95

Cys Asp Glu Phe Ile Asn Val Pro Glu Trp Ser Tyr Ile Val Glu Lys
            100                 105                 110

Ala Asn Pro Thr Asn Asp Leu Cys Tyr Pro Gly Ser Phe Asn Asp Tyr
        115                 120                 125

Glu Glu Leu Lys His Leu Leu Ser Arg Ile Asn His Phe Glu Lys Ile
130                 135                 140

Leu Ile Ile Pro Lys Ser Ser Trp Ser Asp His Glu Ala Ser Ser Gly
145                 150                 155                 160

Val Ser Ser Ala Cys Pro Tyr Leu Gly Ser Pro Ser Phe Phe Arg Asn
                165                 170                 175

Val Val Trp Leu Ile Lys Lys Asn Ser Thr Tyr Pro Thr Ile Lys Lys
            180                 185                 190

Ser Tyr Asn Asn Thr Asn Gln Glu Asp Leu Leu Val Leu Trp Gly Ile
        195                 200                 205

His His Pro Asn Asp Ala Ala Glu Gln Thr Arg Leu Tyr Gln Asn Pro
210                 215                 220

Thr Thr Tyr Ile Ser Ile Gly Thr Ser Thr Leu Asn Gln Arg Leu Val
225                 230                 235                 240

Pro Lys Ile Ala Thr Arg Ser Lys Val Asn Gly Gln Ser Gly Arg Met
                245                 250                 255

Glu Phe Phe Trp Thr Ile Leu Lys Pro Asn Asp Ala Ile Asn Phe Glu
            260                 265                 270

Ser Asn Gly Asn Phe Ile Ala Pro Glu Tyr Ala Tyr Lys Ile Val Lys
        275                 280                 285

Lys Gly Asp Ser Ala Ile Met Lys Ser Glu Leu Glu Tyr Gly Asn Cys
290                 295                 300

Asn Thr Lys Cys Gln Thr Pro Met Gly Ala Ile Asn Ser Ser Met Pro
305                 310                 315                 320

Phe His Asn Ile His Pro Leu Thr Ile Gly Glu Cys Pro Lys Tyr Val
```

```
            325                 330                 335
Lys Ser Asn Arg Leu Val Leu Ala Thr Gly Leu Arg Asn Ser Pro Gln
            340                 345                 350

Arg Glu Ser Arg Arg Lys Lys Arg Gly Leu Phe Gly Ala Ile Ala Gly
            355                 360                 365

Phe Ile Glu Gly Gly Trp Gln Gly Met Val Asp Gly Trp Tyr Gly Tyr
            370                 375                 380

His His Ser Asn Glu Gln Gly Ser Gly Tyr Ala Ala Asp Lys Glu Ser
385                 390                 395                 400

Thr Gln Lys Ala Ile Asp Gly Val Thr Asn Lys Val Asn Ser Ile Ile
            405                 410                 415

Asp Lys Met Asn Thr Gln Phe Glu Ala Val Gly Arg Glu Phe Asn Asn
            420                 425                 430

Leu Glu Arg Arg Ile Glu Asn Leu Asn Lys Lys Met Glu Asp Gly Phe
            435                 440                 445

Leu Asp Val Trp Thr Tyr Asn Ala Glu Leu Leu Val Leu Met Glu Asn
            450                 455                 460

Glu Arg Thr Leu Asp Phe His Asp Ser Asn Val Lys Asn Leu Tyr Asp
465                 470                 475                 480

Lys Val Arg Leu Gln Leu Arg Asp Asn Ala Lys Glu Leu Gly Asn Gly
            485                 490                 495

Cys Phe Glu Phe Tyr His Lys Cys Asp Asn Glu Cys Met Glu Ser Ile
            500                 505                 510

Arg Asn Gly Thr Tyr Asn Tyr Pro Gln Tyr Ser Glu Glu Ala Arg Leu
            515                 520                 525

Lys Arg Glu Glu Ile Ser Gly Val Lys Leu Glu Ser Ile Gly Thr Tyr
            530                 535                 540

Gln Ile Val Thr Leu Trp Ala Thr Val Phe Leu Thr Leu Gly Ala Leu
545                 550                 555                 560

Val Ala Gly Ala Lys Val Trp Glu Ile Met Arg Lys Ala Asn Arg Lys
            565                 570                 575

Ser Gln Tyr Lys Arg Thr Asn Thr Glu Pro His Asp Ser Gln Ala Thr
            580                 585                 590

Trp Ile

<210> SEQ ID NO 3
<211> LENGTH: 176
<212> TYPE: PRT
<213> ORGANISM: Lettuce necrotic yellows virus

<400> SEQUENCE: 3

Ser Ala Lys Leu Asn Trp Tyr Arg Ile Thr Phe Asn Asp Thr Val Trp
1               5                   10                  15

Arg Phe Asp Thr Ala Arg Gly Pro Lys Asp Gly Glu Thr Cys Pro Leu
            20                  25                  30

Ile Ala Ser Glu Leu Phe Ser Ser Gly Leu Ser Glu Val Phe Lys Ser
            35                  40                  45

Val Thr Ser Phe Ser Glu Ile Leu Arg Asn Met Glu Ser Arg Gly Tyr
            50                  55                  60

Ile Thr Asn Ile Thr Leu Arg Ala Asp Ser Asp Ile Leu Gly Pro Gly
65                  70                  75                  80
```

Ala Leu Arg Cys Glu Phe Leu Phe Pro Ser Glu Val Phe Ile Pro Thr
                85                  90                  95

Ser His Thr Leu Lys Met Gly Arg Ser Ser Leu Ile Leu Glu Pro His
            100                 105                 110

Leu Val Val Leu Lys Glu Cys Lys Tyr Ile Ser Ser Gly Lys Leu Asp
            115                 120                 125

Ile Gly Ile Ser Ser Ile Glu Ala Thr Ser Val Ala Val Leu Arg Arg
130                 135                 140

Val Lys Gly Pro Ala Phe Ile Gly Cys Met Asp Asp Asn Pro Phe Gly
145                 150                 155                 160

Val Leu Thr Lys Lys Pro Ser Asp Glu Lys Asn Val Leu Ala Ser Lys
                165                 170                 175

<210> SEQ ID NO 4
<211> LENGTH: 252
<212> TYPE: PRT
<213> ORGANISM: Avian influenza virus

<400> SEQUENCE: 4

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
            115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Ala Arg Gln Met Val Gln Ala Met Arg Thr Ile Gly Thr His Pro Ser
        210                 215                 220

Ser Ser Ala Gly Leu Lys Asp Asn Leu Leu Glu Asn Leu Gln Ala Tyr
225                 230                 235                 240

Gln Lys Arg Met Gly Val Gln Met Gln Arg Phe Lys
                245                 250